United States Patent
Zhang et al.

(10) Patent No.: US 10,828,390 B2
(45) Date of Patent: Nov. 10, 2020

(54) BIOMIMETIC CHITOSAN FILLER FOR PREVENTING CAPSULAR CONTRACTURE AND PREPARATION METHOD THEREOF

(71) Applicant: Shanghai Haohai Biological Technology Co., Ltd, Shanghai (CN)

(72) Inventors: Kun Zhang, Shanghai (CN); Wanhua Chen, Shanghai (CN); Bingqian Bu, Shanghai (CN); Jianying Wu, Shanghai (CN); Jundong Zhang, Shanghai (CN); Zhen Chang, Shanghai (CN); Peng Du, Shanghai (CN)

(73) Assignee: SHANGHAI HAOHAI BIOLOGICAL TECHNOLOGY CO., LTD., Shanghai (CN)

( * ) Notice: Subject to any disclaimer, the term of this patent is extended or adjusted under 35 U.S.C. 154(b) by 370 days.

(21) Appl. No.: 15/760,635

(22) PCT Filed: Dec. 25, 2017

(86) PCT No.: PCT/CN2017/118268
§ 371 (c)(1),
(2) Date: Mar. 16, 2018

(87) PCT Pub. No.: WO2019/114029
PCT Pub. Date: Jun. 20, 2019

(65) Prior Publication Data
US 2020/0230287 A1 Jul. 23, 2020

(30) Foreign Application Priority Data

Dec. 13, 2017 (CN) .......................... 2017 1 1324172

(51) Int. Cl.
*A61L 27/20* (2006.01)
*A61L 27/38* (2006.01)
*A61L 27/50* (2006.01)

(52) U.S. Cl.
CPC ........... *A61L 27/20* (2013.01); *A61L 27/3839* (2013.01); *A61L 27/50* (2013.01); *A61L 2300/41* (2013.01); *A61L 2430/04* (2013.01)

(58) Field of Classification Search
CPC ....... A61L 27/20; A61L 27/3839; A61L 27/50
See application file for complete search history.

(56) References Cited

U.S. PATENT DOCUMENTS

| 2008/0075657 A1* | 3/2008 | Abrahams | ............... A61L 24/08 |
| | | | 424/1.11 |
| 2016/0186142 A1* | 6/2016 | Serteyn | ................... A61P 19/10 |
| | | | 424/93.7 |

FOREIGN PATENT DOCUMENTS

| CN | 1517077 A | 8/2004 | |
| CN | 108245709 A | 7/2018 | |
| EP | 1676591 A3 | 9/2006 | |
| WO | WO2014/126370 A1 * | 8/2014 | ............... A61K 9/70 |

* cited by examiner

*Primary Examiner* — Pancham Bakshi
(74) *Attorney, Agent, or Firm* — Bayramoglu Law Offices LLC

(57) ABSTRACT

The present invention relates to the technical field of reconstructive plastic surgery and cosmetology, and particularly to a biomimetic chitosan filler for preventing capsular contracture and preparation method thereof. The biomimetic chitosan filler for preventing capsular contracture includes chitosan gel, cross-linked sodium hyaluronate, surfactant, isoosmotic regulator, autologous adipose-derived stem cells, pH adjusting agent and water. The amount of the pH adjusting agent is to adjust a pH value of the chitosan filler to be within a range of 6.5-7.5. The chitosan filler prepared according to the present invention can reduce the inflammation caused by post-operative silica gel exudation, and prevent the occurrence and development of capsular contracture.

9 Claims, No Drawings

BIOMIMETIC CHITOSAN FILLER FOR PREVENTING CAPSULAR CONTRACTURE AND PREPARATION METHOD THEREOF

CROSS-REFERENCE TO RELATED APPLICATIONS

This application is the national stage entry of International Application No. PCT/CN2017/118268, filed on Dec. 25, 2017, which claims the benefit of priority from Chinese Patent Application No. CN201711324172.4, filed on Dec. 13, 2017, the entire contents of which are incorporated herein by reference.

TECHNICAL FIELD

The present invention relates to the technical field of reconstructive plastic surgery and cosmetology, and particularly to a biomimetic chitosan filler for preventing capsular contracture and preparation method thereof.

BACKGROUND

Prosthesis breast augmentation is popular in reconstructive plastic and cosmetic surgery, although many complications may occur. The capsular contracture is one of the critical issues to be solved. The incidence of capsular contracture occurs in 2.8% to 20.4% cases, so it is the most common complication after breast implant operation. Generally, the capsular contracture refers to the formation of capsule around the prosthesis after the prosthesis breast implant operation. Capsular contracture would cause prosthesis sclerosis, breast ache, and breast deformation, so it seriously affects the patient's quality of life. Therefore, it is of great significance to prevent the occurrence of capsular contracture. The occurrence of capsular contracture depends on many factors. With the progress achieved in the researches, currently, bacterial infection, cell and immunization are considered to be closely related to the occurrence of capsular contracture.

The pathogeny of capsular contracture is as follows.

1. Bacterial infection and biofilms: Capsular contracture is a consequence of an interplay of many factors, and is particularly related to bacterial infection and biofilm stimulation continued for a long period of time resulting from the chronic inflammation after the prosthesis is implanted into the organism. The prosthesis which is regarded as the attachment sites of free bacteria can promote bacterial adhesion, aggregation and the formation of bacterial biofilm. Bacterial biofilm is a highly-organized multicellular population structure, which can effectively resist the phagocytosis of the body's immune defense system and the sterilization effect of antibacterial drugs. It is reported in researches that 45%-60% of the occurrences of capsular contracture are associated with bacterial infection or biofilm. The relevant bacteria mainly include coagulase negative staphylococcus, *Staphylococcus epidermidis, Propionibacterium acnes* and so on. If pathogenic bacteria flora invades the host and adheres to the surface of the prosthesis to form biofilms during the implantation of prosthesis, infection may be caused.

2. Cell differentiation: Capsular contracture is an overfibrosis reaction of the organism after prosthesis implantation. The over-fibrosis reaction is expressed as an activation of myofibroblasts, a loss of regulation due to deposition of extracellular matrix, and excessive tissue atrophy. Capsular contracture tissues are rich in fibroblasts, myofibroblasts and a series of inflammatory cells. Fibroblasts synthesize type I, type III collagen and fibronectin. The number of fibroblasts is also closely related to the severity of capsular contracture. The higher grade of capsular contracture, the larger number of fibroblasts are contained. The α-smooth muscle actin (α-SMA) is an important protein of myofibroblasts and is closely related to the activity of myofibroblasts. The fibroblasts at quiescent state do not express α-smooth muscle actin. Chronic inflammation around the prosthesis can induce the fibroblasts to proliferate and differentiate into α-SMA positive myofibroblasts. The excessive secretion of collagen fibers would cause the formation of capsular contracture of prosthesis, thereby causing breast ache and deformation etc.

3. Immune and signal transduction: The occurrence of capsular contracture is related to a series of chronic inflammation involving a variety of immunologic factors, such as tumor necrosis factor-α (TNF-α), transforming growth factor β1 (TGF-β1), IL-6 (Interleukin-6) and anti-inflammatory cytokines such as IL-10 (Interleukin-10) etc. Each of these immunologic factors is significantly associated with the continued occurrence of inflammation. IL-6 is a potent myofibroblast activator that is specifically expressed in T cells separated from the capsular contracture lumen, this suggests that the number of fibroblasts in the capsular contracture tissue is significantly related to IL-6, and there are potential paracrine signals between fibroblasts and T cells. IL-10 having a strong immunosuppressive effect and anti-fibrosis effect can reduce the production of type I collagen of dermal fibroblasts thereby reducing the degree of tissue fibrosis. TNF-α is one of the key regulators of capsular contracture and is also a key inflammatory factor, which can induce the expression of TGF-β in fibroblasts. The increase of expression of TNF-α is associated with the severity of capsular contracture.

The formation factors of capsule are as follows.

(1) As is found in researches of quality and trait of prosthesis, the breast prosthesis with textured surface has a lower risk of capsular contracture than the smooth breast prosthesis, and silicone gel breast prosthesis feels significantly better than saline breast prosthesis.

(2) Implant location of prosthesis: when the prosthesis was implanted into the interspace of the pectoralis major, the incidence of capsular contracture was significantly lower than implanting the prosthesis into the retromammary interspace.

(3) Hematoma: if the hematocele in surgical area is drained insufficiently and forms hematoma, the incidence of postoperative capsular contracture may be greatly increased.

(4) Infection: the incidence of postoperative capsular contracture may be greatly increased even if recessive infection occurs in the surgical area.

(5) Foreign body: the incidence of postoperative capsular contracture may be increased if the gloves are stained by talcum powder.

The degree of breast capsular contracture may be graded into four grades: grade I, the breast is normally soft; grade II, the breast is a little firm, the breast prosthesis can be felt by hand but appears normal; grade III, the breast is firm, the breast prosthesis can be felt by hand easily and appears abnormal; grade IV, the breast is hard, painful to the touch, sensitive, and the prosthesis deforms. At present, the measures to prevent capsular contracture mainly include: selecting high-quality prosthesis with textured surface; washing the gloves during operation to prevent the prosthesis from contacting foreign body; paying attention to hemostasis and placing drainage tube for 3~5 days after operation; using antibiotics for preventive purpose; preferably selecting the interspace of pectoralis major as the implant location of prosthesis; orally taking Traditional Chinese Patent Medicine (TCPM) such as Fukang tablets etc. to improve the human environment; massaging breast under the guidance of doctors.

Currently, the measures for preventing capsular contracture mainly include the following.

1. In view of the possibility of bacterial infection during prosthesis implantation, the following methods are recommended to prevent capsular contracture, such as the use of antibiotics for preventive purpose, strict aseptic operation, and washing with antibiotics during the operation to reduce bacterial adhesion. However, with the bacterial drug resistance, the long-term use may not be effective. The anti-bacteria and anti-adhesion prosthesis which might be developed in the future may be able to inhibit the occurrence of capsular contracture.

2. Leukotriene receptor antagonists is used to reduce the incidence of capsular contracture by altering the inflammatory response. Each ligand molecule in the TGF-β superfamily contains seven highly conserved cysteine residues. The leukotriene receptor antagonists can inhibit the expression of cysteinyl leukotriene receptor and plays an important role in the prevention and treatment of capsular contracture. The major mechanism of the action of the leukotriene receptor antagonists is to prevent the capsular contracture by altering the inflammatory cascade and preventing severe fibrotic reactions. Cysteine leukotriene receptor-2 (CysLTR2) messenger RNA and protein are highly expressed in macrophages and myofibroblasts of capsular contracture tissues, this suggests that CysLTR2 is likely involve in the development of capsular contracture. Zafirlukast can reduce the incidence of capsular contracture by inhibiting the activity of myofibroblasts and performing its anti-inflammatory effect.

3. Botulinum toxin type A(BTX-A) can reduce the number of inflammatory cells, inhibit the expression of TGF-β and inhibit the development of capsular contracture. BTX-A inhibits the signaling pathway of TGF-β and thus decreases the production of type I collagen and type III collagen. These results directly or indirectly indicate that BTX-A inhibits the signaling of TGF-β, thereby reducing the expression of collagen and ultimately inhibiting occurrence of capsular contracture around prosthesis.

4. Statins have multiple functions such as immune regulation and anti-fibrosis etc. and can inhibit the development of capsular contracture. CTGF (Connective Tissue Growth Factor) can stimulate the proliferation of fibroblast and the deposition of collagen, and work together with TGF-β to promote tissue fibrosis. Hydroxymethyl glutaryl coenzyme A reductase inhibitors can inhibit the production of fibrosis-related factors.

5. Tamoxifen, an estrogen receptor antagonist, can reduce the production of TGF-β and the contractility of myofibroblasts, and is used in the prevention of capsular contracture.

6. Anti-adhesion barriers (AABS) can reduce the occurrence of capsular contracture by inhibiting the inflammatory and fibrosis reactions. In detail, the anti-adhesion barriers mainly reduce the incidence and development of capsular contracture by inhibiting the collagen-producing pathways.

7. Acellular dermal matrix (ADM) can slow down the process of human tissue fibrosis, thereby reducing the incidence of capsular contracture.

8. The formation of capsular contracture is related to collagen deposition. The collagenase can inhibit the transformation from fibroblasts into myofibroblasts, dissolve the fibrotic capsular membrane around the prosthesis, reduce the thickness of capsule, and thereby preventing the occurrence of capsular contracture. At present, the mechanism of capsular contracture is related to the development of inflammatory response, and the process of capsular contracture involves the processes of bacterial infection, cell differentiation, immune response and signal transduction etc.

SUMMARY OF THE INVENTION

The present invention mainly provides a biomimetic chitosan filler for preventing capsular contracture and a preparation method thereof. The filler can reduce the inflammation caused by post-operative silicon exudation and prevent the occurrence and development of capsular contracture.

The technical solutions are as follows. A biomimetic chitosan filler for preventing capsular contracture includes a chitosan gel, a cross-linked sodium hyaluronate, a surfactant, an isoosmotic regulator, autologous adipose-derived stem cells, a pH adjusting agent and water. The amount of the pH adjusting agent is to adjust a pH value of the chitosan filler to be within a range of 6.5-7.5.

The biomimetic chitosan filler for preventing capsular contracture includes 0.005-10 wt ‰ of the chitosan gel, 0.005-10 wt ‰ of the cross-linked sodium hyaluronate, 0.5-100 wt ‰ of the surfactant, 0.05-50 wt ‰ of the isoosmotic regulator, $1\times10^5$-$1\times10^{10}$ cells/3 mL of the autologous adipose-derived stem cells, the pH adjusting agent and the rest amount is water. The amount of the pH adjusting agent is to adjust the pH value of the chitosan filler to be within a range of 6.5-7.5.

Preferably, the chitosan gel is a hydroxybutyl chitosan gel.

Preferably, the cross-linked sodium hyaluronate is a cross-linked sodium hyaluronate in molecular weight of $2.5\times10^3$-$6.0\times10^3$ kDa.

Preferably, the surfactant is a polyol; the isoosmotic regulator is one or more item selected from sodium chloride, potassium chloride or magnesium chloride.

Preferably, the surfactant is one or more item selected from polyethylene glycol, butylene glycol or tween 80; the isoosmotic regulator is a mixture of sodium chloride and potassium chloride, wherein the sodium chloride accounts for 40-85 wt % of a total amount of the isoosmotic regulator, and the potassium chloride accounts for 15-60 wt % of the total amount of the isoosmotic regulator.

Preferably, the pH adjusting agent is one or more item selected from boric acid, sodium borate, phosphate buffer, sodium hydroxide, hydrochloric acid, citric acid or sodium citrate.

Preferably, osmolality of the biomimetic chitosan filler is in a range of 270-320 mOsmol/Kg.

A preparation method of the biomimetic chitosan filler for preventing capsular contracture including the following steps:

(1) weighing 40-60 wt % of water according to a ratio of a formula, adding the weighted water together with a chitosan gel, a cross-linked sodium hyaluronate, a surfactant, an isoosmotic regulator, and autologous adipose-derived stem cells to a container according to the ratio of the formula; uniformly stirring the components and adding a pH adjusting agent to adjust a pH value to be within a range of 6.5-7.5; and performing a sterilization.

(2) further adding a rest amount of water, then performing proper shaking, sterilization and subpackaging.

Preferably, in step (1), a stirring speed is in a range of 100-200 rpm, a stirring time is in a range of 3-6 hours and a temperature is in a range of 15-25° C.; the sterilizations in step (1) and step (2) are both to use a 0.2 µm filter membrane to filter and sterilize.

The present invention has the following advantages by using the forgoing solutions.

Autologous adipose-derived stem cells (ADSCs) have been isolated and studied since 2001, and now are the most widely used adult stem cells in the field of tissue engineering and regenerative medicine. Compared with stem cells from other sources, ADSCs have the following unique advantages, such as abundant sources, convenient sampling, high proliferative activity and multidirectional differentiation potential etc. The application of autologous adipose transplantation technique in the field of surgery, trauma, repair and reconstruction is also becoming more and more extensive.

Chitosan gel is in a liquid state at room temperature and become gelate in vivo after implantation, so the chitosan gel can act as a good physical barrier. On the one hand, the cross-linked sodium hyaluronate with high molecular weight is combined with non-covalent bonds of the chitosan to realize a stabilization function. On the other hand, the cross-linked sodium hyaluronate with high molecular weight plays a role in blocking inflammation-related receptors such as TRL4 (Toll-like receptor 4) and inhibiting the production and infiltration of inflammatory factors IL-6 and TNF-α. Autologous adipose stem cell hormone directly plays a role of anti-inflammatory. Applying the present invention to clinical orthopedic breast augmentation surgery can reduce the inflammation caused by post-operative silica gel exudation and prevent the occurrence and development of capsular contracture.

DETAILED DESCRIPTION OF THE INVENTION

Embodiment 1

A biomimetic chitosan filler for preventing capsular contracture includes 10 wt ‰ hydroxybutyl chitosan gel, 10 wt ‰ cross-linked sodium hyaluronate in molecular weight of $2.5 \times 10^3$-$6.0 \times 10^3$ kDa, 0.5 wt ‰ polyethylene glycol, 0.02 wt ‰ sodium chloride, 0.03 wt ‰ potassium chloride, $1 \times 10^{10}$ autologous adipose-derived stem cells and phosphate buffer, the rest amount is water for injection. The amount of phosphate buffer is to adjust the pH value of the chitosan filler to 7.0, the final volume of chitosan filler is 3 mL, and the biomimetic chitosan filler has an osmolality of 300 mOsmol/Kg.

The preparation method of the above-mentioned chitosan filler is as follows:

(1) 50 wt % water for injection is weighed according to the ratio of formula. The weighted water is added into a container together with the chitosan gel, the cross-linked sodium hyaluronate, the surfactant, the isoosmotic regulator and autologous adipose-derived stem cells according to the ratio of formula. After that, uniform stirring is performed under the conditions of 150 rpm of speed, 5 h of time, 20° C. of temperature. Then pH adjusting agent is added to adjust pH value to 7.0, and 0.2 µm filter membrane is used to filter and sterilize.

(2) The rest volume of water for injection is further added, then proper shaking is performed, and 0.2 µm filter membrane is used to filter and sterilize, then subpackaging is performed.

Embodiment 2

A biomimetic chitosan filler for preventing capsular contracture includes 0.005 wt ‰ hydroxybutyl chitosan gel, 5 wt ‰ cross-linked sodium hyaluronate in molecular weight of $2.5 \times 10^3$-$6.0 \times 10^3$ kDa, 100 wt ‰ mixture of butylene glycol and tween 80, 50 wt ‰ magnesium chloride, $1 \times 10^5$ autologous adipose-derived stem cells and boric acid, the rest amount is water for injection. The amount of boric acid is to adjust the pH value of the chitosan filler to 6.5, the final volume of chitosan filler is 3 mL, and the biomimetic chitosan filler has an osmolality of 270 mOsmol/Kg.

The preparation method of the above-mentioned chitosan filler is as follows:

(1) 40 wt % water for injection is weighed according to the ratio of formula. The weighted water is added into a container together with the chitosan gel, the cross-linked sodium hyaluronate, the surfactant, the isoosmotic regulator and autologous adipose-derived stem cells according to the ratio of formula. After that, uniform stirring is performed under the conditions of 200 rpm of speed, 6 h of time, 25° C. of temperature. Then pH adjusting agent is added to adjust pH value to 6.5, and 0.2 µm filter membrane is used to filter and sterilize.

(2) The rest volume of water for injection is further added, then proper shaking is performed, and 0.2 µm filter membrane is used to filter and sterilize, then subpackaging is performed.

Embodiment 3

A biomimetic chitosan filler for preventing capsular contracture includes 5 wt ‰ chitosan gel, 0.005 wt ‰ cross-linked sodium hyaluronate in molecular weight of $2.5 \times 10^3$-$6.0 \times 10^3$ kDa, 50 wt ‰ tween 80, 20 wt ‰ potassium chloride, $1 \times 10^{10}$ autologous adipose-derived stem cells and hydrochloric acid, the rest amount is water for injection. The amount of the hydrochloric acid is to adjust the pH value of the chitosan filler to 7.5, the final volume of chitosan filler is 3 mL, and the biomimetic chitosan filler has an osmolality of 320 mOsmol/Kg.

The preparation method of the above-mentioned chitosan filler is as follows:

(1) 60 wt % water for injection is weighed according to the ratio of formula. The weighted water is added into a container together with the chitosan gel, the cross-linked sodium hyaluronate, the surfactant, the isoosmotic regulator and autologous adipose-derived stem cells according to the ratio of formula. After that, uniform stirring is performed under the conditions of 100 rpm of speed, 3 h of time, 15° C. of temperature. Then pH adjusting agent is added to adjust pH value to 7.5, and 0.2 µm filter membrane is used to filter and sterilize.

(2) The rest volume of water for injection is further added, then proper shaking is performed, and 0.2 µm filter membrane is used to filter and sterilize, then subpackaging is performed.

Embodiment 4

A biomimetic chitosan filler for preventing capsular contracture includes 1 wt ‰ chitosan gel, 1 wt ‰ cross-linked sodium hyaluronate in molecular weight of $2.5 \times 10^3$-$6.0 \times 10^3$ kDa, 20 wt ‰ mixture of polyethylene glycol and butanediol, 5 wt ‰ sodium chloride, $1 \times 10^{10}$ autologous adipose-derived stem cells and sodium citrate, the rest amount is water for injection. The amount of sodium citrate is to adjust the pH value of the chitosan filler to 7.0, the final volume of chitosan filler is 3 mL, and the biomimetic chitosan tiller has an osmolality of 280 mOsmol/Kg.

The preparation method of the above chitosan fillers is as follows:

(1) 50 wt % water for injection is weighed according to the ratio of formula. The weighted water is added into a container together with the chitosan gel, the cross-linked sodium hyaluronate, the surfactant, the isoosmotic regulator and autologous adipose-derived stem cells according to the ratio of formula. After that, uniform stirring is performed under the conditions of 150 rpm of speed, 4 h of time, 18° C. of temperature. Then pH adjusting agent is added to adjust pH value to 7.0, and 0.2 μm filter membrane is used to filter and sterilize.

(2) The rest volume of water for injection is further added, then proper shaking is performed, and 0.2 μm filter membrane is used to filter and sterilize, then subpackaging is performed.

Comparative Example 1

In this comparative example, the difference from embodiment 1 is that no adipose-derived stem cells are contained, and the specific formula is as follows.

A chitosan filler includes 10 wt ‰ hydroxybutyl chitosan gel, 10 wt ‰ cross-linked sodium hyaluronate in molecular weight of $2.5 \times 10^3$-$6.0 \times 10^3$ kDa, 0.5 wt ‰ polyethylene glycol, 0.02 wt ‰ sodium chloride, 0.03 wt ‰ potassium chloride and phosphate buffer, the rest amount is water for injection. The amount of phosphate buffer is to adjust the pH value of the chitosan filler to 7.0, the final volume of chitosan filler is 3 mL.

Comparative Example 2

In this comparative example, the difference from embodiment 1 is that no adipose-derived stem cells and chitosan are contained, and the specific formula is as follows.

A filler includes 10 wt ‰ cross-linked sodium hyaluronate in molecular weight of $2.5 \times 10^3$-$6.0 \times 10^3$ kDa, 0.5 wt ‰ polyethylene glycol, 0.02 wt ‰ sodium chloride, 0.03 wt ‰ potassium chloride and phosphate buffer, the rest amount is water for injection. The amount of the phosphate buffer is to adjust the value of the chitosan filler to 7.0, the final volume of chitosan filler is 3 mL.

Animal Experiment

1. Experimental Method:

Eighteen female SD rats were chosen as subjects for the experiment, and were randomly divided into three groups i.e. group A, group B, and group C. 1 wt % amobarbital sodium was injected into the rats at abdominal cavity for anesthesia at 70 mg/kg. Longitudinal incisions with length of 2 cm were respectively made on both sides of the back midline of the SD rats at a position 1 cm apart from the midline, and symmetrical cavities were formed under the latissimus dorsi by stripping. A 10 ml round silicone gel prosthesis (produced by Beijing Research & Design institute of Rubber Products) were placed under the latissimus dorsi on each side of the rats. The left side of each rat was the experimental group, the right side of each rat was the control group. In group A, the biomimetic chitosan filler prepared in embodiment 1 was injected into the left stripping cavity of rats, and the right side was untreated. In group B, the chitosan gel without adipose-derived stem cells prepared in comparative example 1 was injected into the left stripping cavity of rats, and the right side was untreated. In group C, the sodium hyaluronate gel without chitosan and stem cells prepared in comparative example 2 was injected into the left stripping cavity of rats, and the right side was untreated. At 4, 8 and 12 weeks after surgery, the capsules were excised and examined by histological examination by groups, and the thickness and the areal density of type I and type III collagen of the capsules were measured. The data was represented by x±s, and the t-test of paired data was performed using Spss11.0 statistical software.

2. Experimental Results:

TABLE 1

The capsule thickness comparison on the experimental side and control side at 4 weeks after surgery

| group | collagen type | experimental side(μm) | control side(μm) | P value |
|---|---|---|---|---|
| A | type I | 0.063 ± 0.007 | 0.198 ± 0.063 | P < 0.01 |
|   | type III | 0.089 ± 0.009 | 0.208 ± 0.033 | P < 0.01 |
| B | type I | 0.098 ± 0.011 | 0.179 ± 0.066 | P < 0.01 |
|   | type III | 0.099 ± 0.007 | 0.191 ± 0.067 | P < 0.01 |
| C | type I | 0.187 ± 0.028 | 0.189 ± 0.083 | P > 0.05 |
|   | type III | 0.179 ± 0.006 | 0.177 ± 0.036 | P > 0.05 |

TABLE 2

The capsule thickness comparison on the experimental side and control side at 8 weeks after surgery

| group | collagen type | experimental side(μm) | control side(μm) | P value |
|---|---|---|---|---|
| A | type I | 0.031 ± 0.045 | 0.198 ± 0.063 | P < 0.01 |
|   | type III | 0.023 ± 0.005 | 0.208 ± 0.033 | P < 0.01 |
| B | type I | 0.074 ± 0.004 | 0.179 ± 0.066 | P < 0.01 |
|   | type III | 0.077 ± 0.007 | 0.191 ± 0.067 | P < 0.01 |
| C | type I | 0.158 ± 0.004 | 0.189 ± 0.083 | P > 0.05 |
|   | type III | 0.165 ± 0.003 | 0.177 ± 0.036 | P > 0.05 |

TABLE 3

The capsule thickness comparison on the experimental side and control side at 12 weeks after surgery

| group | collagen type | experimental side(μm) | control side(μm) | P value |
|---|---|---|---|---|
| A | type I | 0.007 ± 0.006 | 0.198 ± 0.063 | P < 0.01 |
|   | type III | 0.005 ± 0.008 | 0.208 ± 0.033 | P < 0.01 |
| B | type I | 0.029 ± 0.015 | 0.179 ± 0.066 | P < 0.01 |
|   | type III | 0.038 ± 0.006 | 0.191 ± 0.067 | P < 0.01 |
| C | type I | 0.133 ± 0.007 | 0.189 ± 0.083 | P > 0.05 |
|   | type III | 0.139 ± 0.008 | 0.177 ± 0.036 | P > 0.05 |

As can be seen from Tables 1-3, comparing group A and group B, the addition of adipose-derived stem cells in group A can reduce inflammation caused by silicone exudation after surgery, and has a significant effect on the prevention of capsular contracture. Comparing group B and group C, since chitosan can play a good role in physical barrier, it can block inflammation-related receptors, and inhibit inflammation.

For those skilled in the art, various corresponding changes and variations may be derived according to the foregoing technical solutions and concepts, and all of these changes and variations should fall within the protection scope of the appended claims of the present invention.

What is claimed is:

1. A biomimetic chitosan filler for preventing capsular contracture comprising: a chitosan gel, a cross-linked sodium hyaluronate, a surfactant, an isoosmotic regulator, autologous adipose-derived stem cells, a pH adjusting agent and water;
wherein an amount of the pH adjusting agent is to adjust a pH value of the biometic chitosan filler to be within a range of 6.5-7.5;
wherein the biomimetic chitosan filler has 0.005-10 wt ‰ of the chitosan gel, 0.005-10 wt ‰ of the cross-linked sodium hyaluronate, 0.5-100 wt ‰ of the surfactant, 0.05-50 wt ‰ of the isoosmotic regulator, $1\times10^5$-$1\times10^{10}$ cells/3 mL of the autologous adipose-derived stem cells, pH adjusting agent and a rest amount is water.

2. The biomimetic chitosan filler for preventing capsular contracture of claim 1, wherein the chitosan gel is a hydroxybutyl chitosan gel.

3. The biomimetic chitosan filler for preventing capsular contracture of claim 1, wherein the cross-linked sodium hyaluronate is a cross-linked sodium hyaluronate having a molecular weight of $2.5\times10^3$-$6.0\times10^3$ kDa.

4. The biomimetic chitosan filler for preventing capsular contracture of claim 1, wherein the surfactant is a polyol, the isoosmotic regulator is one or more items selected from the group consisting of sodium chloride, potassium chloride, and magnesium chloride.

5. The biomimetic chitosan filler for preventing capsular contracture of claim 4,
wherein the surfactant is one or more items selected from the group consisting of polyethylene glycol, butylene glycol, and tween 80;
the isoosmotic regulator is a mixture of sodium chloride and potassium chloride, wherein the sodium chloride accounts for 40-85 wt % of a total amount of the isoosmotic regulator, and the potassium chloride accounts for 15-60 wt % of the total amount of the isoosmotic regulator.

6. The biomimetic chitosan filler for preventing capsular contracture of claim 1, wherein the pH adjusting agent is one or more items selected from the group consisting of boric acid, sodium borate, phosphate buffer, sodium hydroxide, hydrochloric acid, citric acid, and sodium citrate.

7. The biomimetic chitosan filler for preventing capsular contracture of claim 1, wherein the chitosan filler has an osmolality of 270-320 mOsmol/Kg.

8. A preparation method of the biomimetic chitosan filler for preventing capsular contracture of claim 1, comprising the following steps:
(1) weighing 40-60 wt of water according to a ratio of a formula;
adding the weighted water together with the chitosan gel, the cross-linked sodium hyaluronate, the surfactant, the isoosmotic regulator, and the autologous adipose-derived stem cells to a container according to the ratio of the formula and uniformly stirring to form a mixture;
adding the pH adjusting agent to the mixture to adjust the pH value to be within the range of 6.5-7.5; and performing a sterilization;
(2) further adding a rest amount of water, then performing proper shaking, sterilization and subpackaging.

9. The preparation method of the biomimetic chitosan filler for preventing capsular contracture of claim 8, wherein in step (1), a stirring speed is in a range of 100-200 rpm;
a stirring time is in a range of 3-6 hours;
a temperature is in a range of 15-25° C.; and
the sterilizations in step (1) and step (2) are both to use a 0.2 μm filter membrane to filter and sterilize.

* * * * *